(12) United States Patent
Parker et al.

(10) Patent No.: US 8,945,216 B2
(45) Date of Patent: Feb. 3, 2015

(54) OBJECTIVE FITTING OF A HEARING PROSTHESIS

(75) Inventors: John Parker, Roseville (AU); Herbert Baechler, Meilen (CH); Markus Haller, Yens (CH)

(73) Assignee: Cochlear Limited, Macquarie University, NSW (AU)

( * ) Notice: Subject to any disclaimer, the term of this patent is extended or adjusted under 35 U.S.C. 154(b) by 1050 days.

(21) Appl. No.: 12/935,901

(22) PCT Filed: Mar. 31, 2009

(86) PCT No.: PCT/US2009/038932
§ 371 (c)(1),
(2), (4) Date: Apr. 20, 2011

(87) PCT Pub. No.: WO2009/124035
PCT Pub. Date: Oct. 8, 2009

(65) Prior Publication Data
US 2011/0190882 A1     Aug. 4, 2011

Related U.S. Application Data

(60) Provisional application No. 61/041,185, filed on Mar. 31, 2008.

(51) Int. Cl.
*A61F 2/18* (2006.01)
*H04R 25/00* (2006.01)
*A61M 5/142* (2006.01)

(52) U.S. Cl.
CPC .............. *H04R 25/00* (2013.01); *H04R 25/606* (2013.01); *H04R 25/70* (2013.01); *A61M 5/14276* (2013.01); *A61M 2205/05* (2013.01); *A61M 2210/0662* (2013.01); *H04R 2460/13* (2013.01)
USPC .......................................................... 623/10

(58) Field of Classification Search
USPC ............................................... 623/10; 600/27
See application file for complete search history.

(56) References Cited

U.S. PATENT DOCUMENTS

| 4,944,301 | A  | * | 7/1990  | Widin et al. ............... 607/57    |
| 5,277,694 | A  | * | 1/1994  | Leysieffer et al. ........... 600/25   |
| 5,999,856 | A  | * | 12/1999 | Kennedy ..................... 607/57   |
| 6,010,532 | A  | * | 1/2000  | Kroll et al. ................. 623/10  |
| 6,491,722 | B1 | * | 12/2002 | Kroll et al. ................. 623/10  |
| 6,807,445 | B2 | * | 10/2004 | Baumann et al. ............. 607/57    |

(Continued)

FOREIGN PATENT DOCUMENTS

EP     0836363       4/1998
WO     WO 98/36711 A1    8/1998

OTHER PUBLICATIONS

International Search Report of PCT/US2009/038932, mailed Jun. 5, 2009.

(Continued)

*Primary Examiner* — Suzette J Gherbi

(57) ABSTRACT

A system for fitting a hearing prosthesis to a recipient. The system comprises a stimulation arrangement configured to at least one of mechanically and acoustically stimulate the recipient's inner ear based on an input signal; a neural response detection arrangement configured to detect the recipient's neural responses to the stimulation; and a processor configured to assess the recipient's neural responses, and to adjust operation of the hearing prosthesis based on the assessment of the neural responses.

20 Claims, 11 Drawing Sheets

(56) References Cited

U.S. PATENT DOCUMENTS

| | | | |
|---|---|---|---|
| 7,187,778 B2* | 3/2007 | Basseas | 381/314 |
| 7,376,563 B2* | 5/2008 | Leysieffer et al. | 704/271 |
| 8,396,239 B2* | 3/2013 | Fay et al. | 381/326 |
| 2002/0012438 A1* | 1/2002 | Leysieffer et al. | 381/312 |
| 2002/0026091 A1* | 2/2002 | Leysieffer | 600/25 |
| 2002/0138115 A1* | 9/2002 | Baumann et al. | 607/57 |
| 2005/0015133 A1 | 1/2005 | Ibrahim et al. | |

OTHER PUBLICATIONS

Supplementary European Search Report mailed on Mar. 3, 2011, in European Application No. 09727686.9 (5 Pages).

Written Opinion issued in PCT/US2009/038932, mailed Sep. 30, 2009.

* cited by examiner

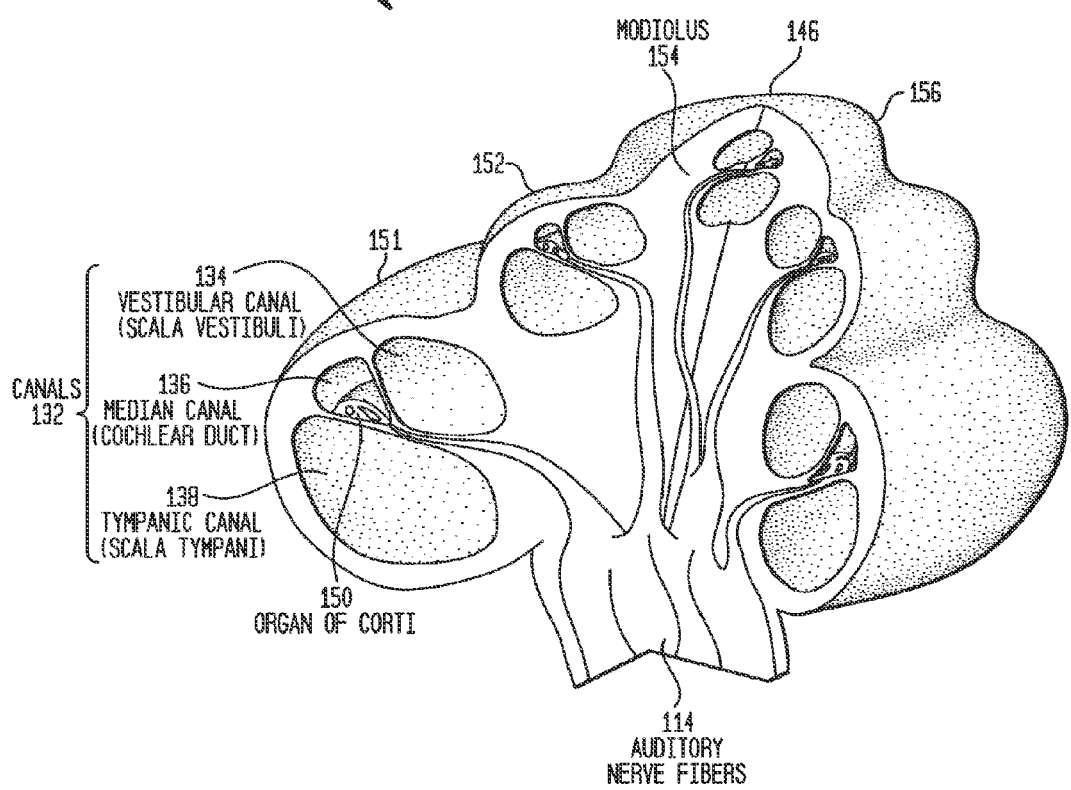

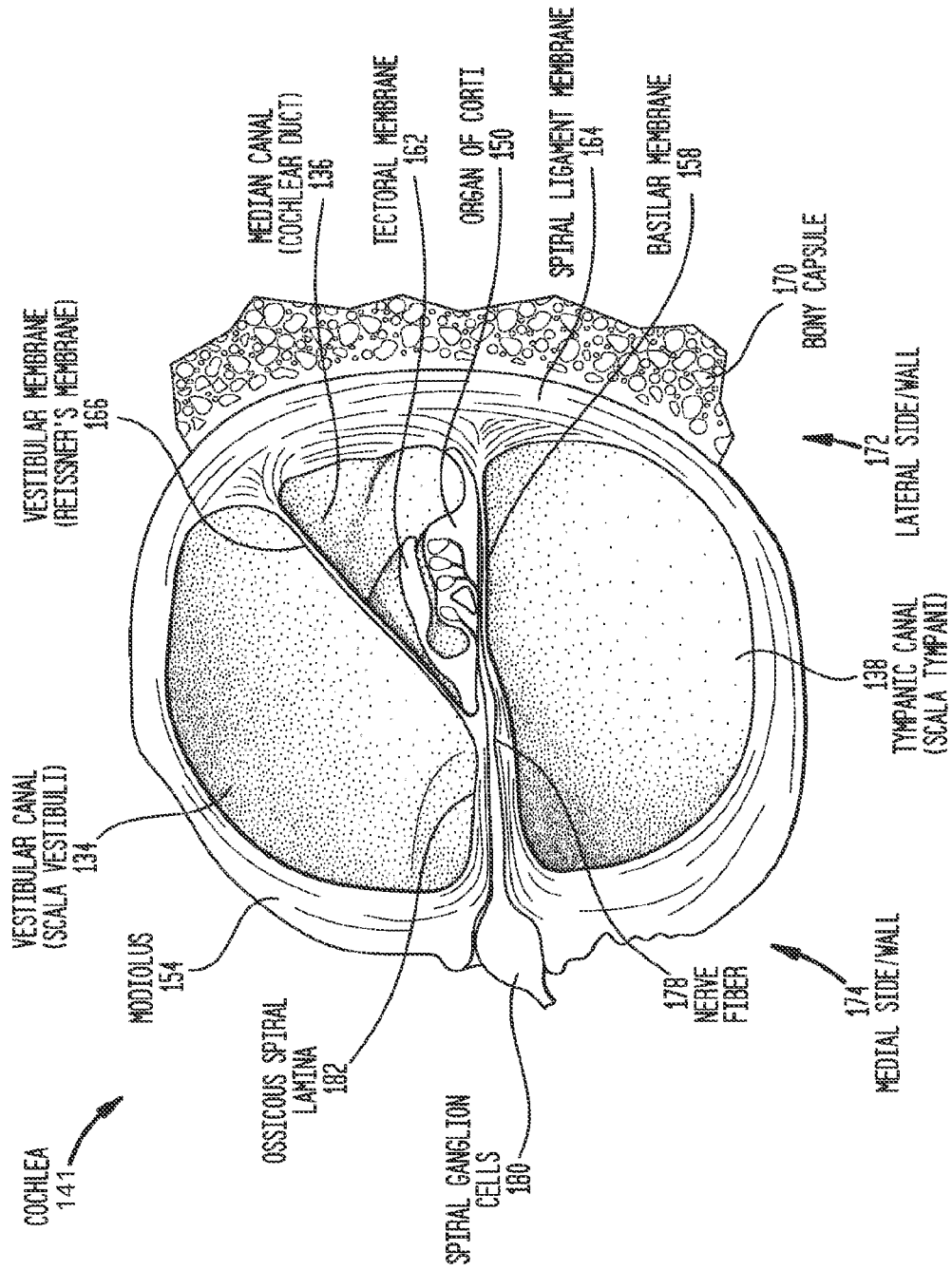

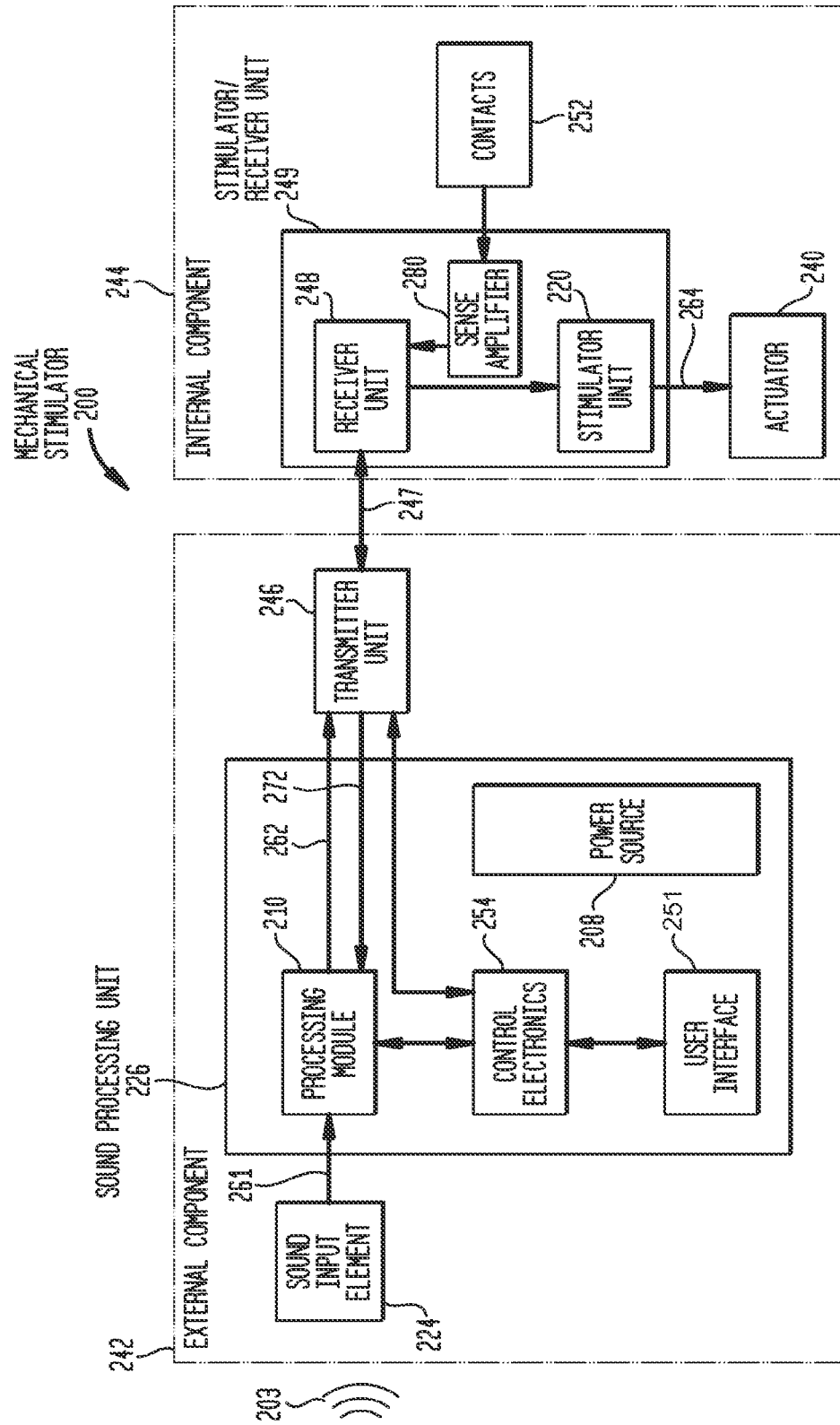

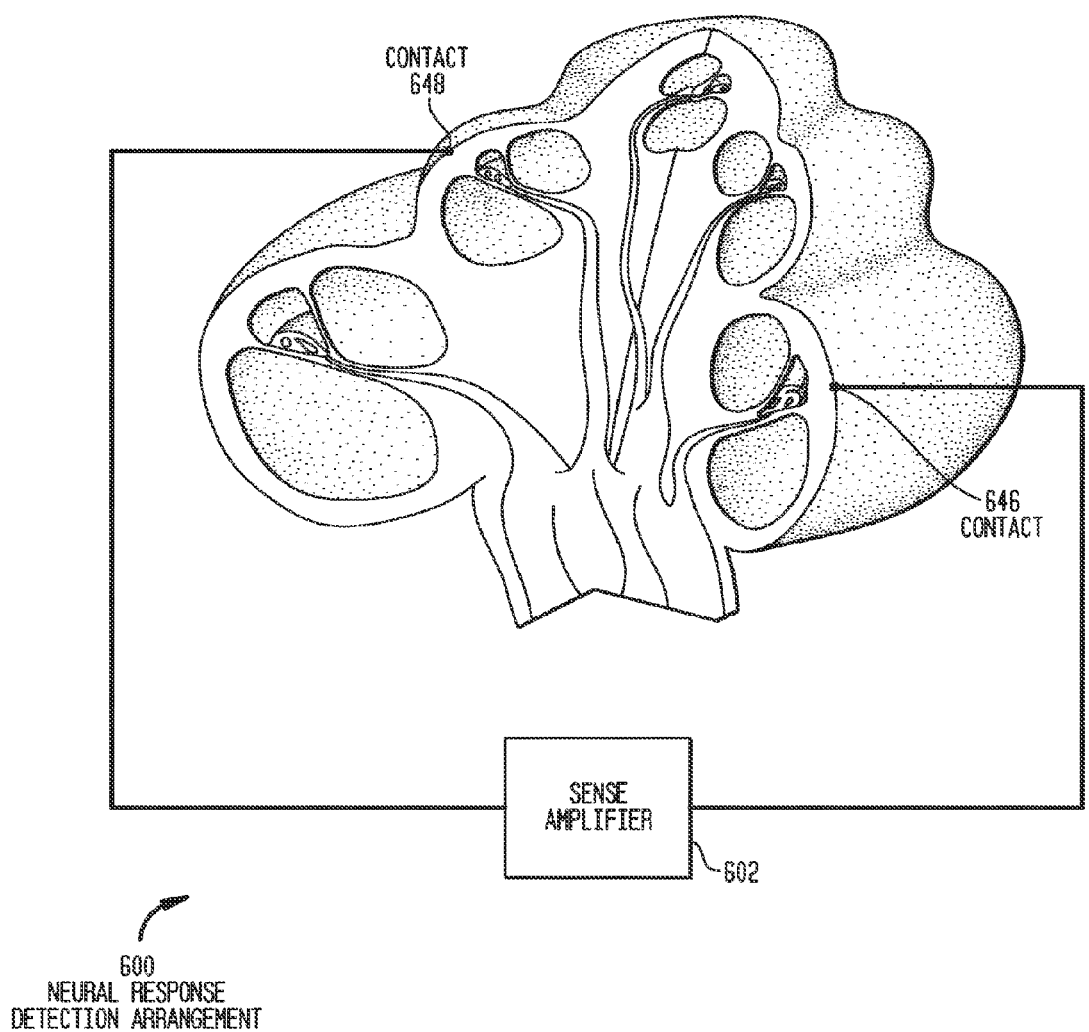

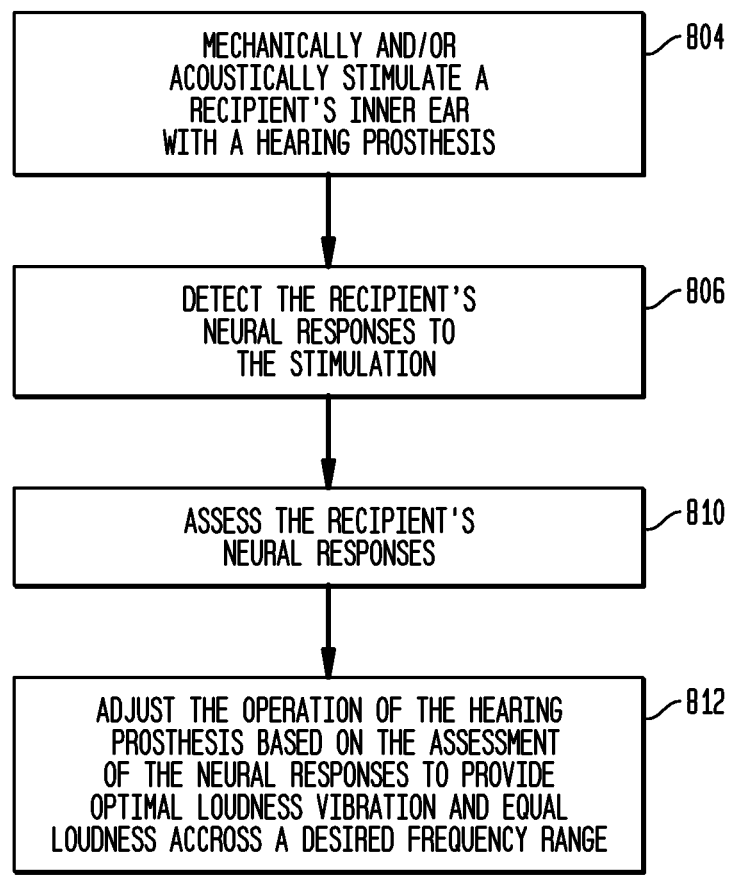

OBJECTIVE FITTING OF A HEARING PROSTHESIS

The present application is a National Stage Application of International Application No. PCT/US09/38932, filed Mar. 31, 2009, and claims the benefit of U.S. Provisional Patent Application 61/041,185; filed Mar. 31, 2008. The contents of these applications is hereby incorporated by reference herein.

BACKGROUND

1. Field of the Invention

The present invention relates generally to hearing prostheses, and more particularly, to objective fitting of a hearing prosthesis.

2. Related Art

Hearing loss, which may be due to many different causes, is generally of two types, conductive and sensorineural. In some cases, an individual may have hearing loss of both types. In many people who are profoundly deaf, however, the reason for their deafness is sensorineural hearing loss. Sensorineural hearing loss occurs when there is damage to the inner ear, or to the nerve pathways from the inner ear to the brain. As such, those suffering from sensorineural hearing loss are thus unable to derive suitable benefit from conventional acoustic hearing aids. As a result, hearing prostheses that deliver electrical stimulation to nerve cells of the recipient's auditory system have been developed to provide persons having sensorineural hearing loss with the ability to perceive sound. Such electrically-stimulating hearing prostheses deliver electrical stimulation to nerve cells of the recipient's auditory system.

As used herein, a recipient's auditory system includes all sensory system components used to perceive a sound signal, such as hearing sensation receptors, neural pathways, including the auditory nerve and spiral ganglion cells, and regions of the brain used to sense sounds. Electrically-stimulating hearing prostheses include, for example, auditory brain stimulators and cochlear prostheses (commonly referred to as cochlear prosthetic devices, cochlear implants, cochlear devices, and the like; simply "cochlear implants" herein.)

Most sensorineural hearing loss is due to the absence or destruction of the cochlea hair cells which transduce acoustic signals into nerve impulses. It is for this purpose that cochlear implants have been developed. Cochlear implants electrically stimulate a recipient's cochlea by directly delivering direct electrical stimulation signals to the auditory nerve cells, thereby bypassing absent or defective hair cells that normally transduce acoustic vibrations into neural activity. Such devices generally use an electrode array implanted in the cochlea to differentially activate auditory neurons that normally encode differential pitches of sound.

In contrast to sensorineural hearing loss, conductive hearing loss occurs when the normal mechanical pathways used to provide sound to hair cells in the cochlea are impeded, for example, by damage to the ossicular chain or to the ear canal. Individuals who suffer from conductive hearing loss typically have some form of residual hearing because the hair cells in the cochlea are undamaged. As a result, individuals suffering from conductive hearing loss typically receive an acoustic hearing aid. Acoustic hearing aids stimulate an individual's cochlea by providing an amplified sound to the cochlea, where the amplified sound causes mechanical motion of the cochlear fluid.

Unfortunately, not all individuals who suffer from conductive hearing loss are able to derive suitable benefit from hearing aids. For example, some individuals are prone to chronic inflammation or infection of the ear canal and cannot wear hearing aids. Similarly, hearing aids are typically unsuitable for individuals who have malformed or damaged outer/middle ears.

Those individuals who suffer conductive hearing loss, but cannot derive suitable benefit from hearing aids may benefit from devices which simulate natural hearing by generating displacement of the inner ear fluid, as occurs in normal hearing, without the need for operable outer and/or middle ears. Once such device is sometimes referred to as a mechanical stimulator herein. Mechanical stimulators are configured to generate a volumetric displacement of a recipient's inner fluid. This inner ear fluid displacement generates a traveling wave on the recipient's basilar membrane, thereby evoking a hearing response by the recipient.

Generally there is a need to fit mechanical stimulators, acoustic hearing aids and other hearing prostheses to a particular recipient. These fitting procedures generally rely upon interactive communication between an audiologist and the recipient.

SUMMARY

In one aspect of the invention, a system for fitting a hearing prosthesis to a recipient is provided. The system comprises: a stimulation arrangement configured to at least one of mechanically and acoustically stimulate the recipient's inner ear based on an input signal; a neural response detection arrangement configured to detect the recipient's neural responses to the stimulation; and a processor configured to assess the recipient's neural responses, and to adjust the operation of the hearing prosthesis based on the assessment of the neural responses.

In another aspect of the invention, a hearing prosthesis is provided. The hearing prosthesis comprises: a stimulation arrangement configured to at least one of mechanically and acoustically stimulate the recipient's inner ear based on an input signal; a neural response detection arrangement configured to detect the recipient's neural responses to the stimulation; and a processor configured to assess the recipient's neural responses, and to adjust the operation of the hearing prosthesis based on the assessment of the neural responses.

In a still other aspect, a method for fitting a hearing prosthesis to a recipient is provided. The method comprises: at least one of mechanically and acoustically stimulating the recipient's inner ear; detecting the recipient's neural responses to the stimulation; assessing the recipient's neural responses; and adjusting the operation of the hearing prosthesis based on the assessment of the neural responses.

BRIEF DESCRIPTION OF THE DRAWINGS

Illustrative embodiments of the present invention are described herein with reference to the accompanying drawings, in which:

FIG. 1B is a perspective, partially cut-away view of a cochlea exposing the canals and nerve fibers of the cochlea;

FIG. 1C is a cross-sectional view of one turn of the canals of a human cochlea;

FIG. 2A is a functional block diagram illustrating a hearing prosthesis in accordance with embodiments of the present invention;

FIG. 6 is a perspective, partially cut-away view of a cochlea illustrating the position of electrical contacts, in accordance with embodiments of the present invention;

FIG. 8 is a flowchart illustrating the operations performed by a hearing prosthesis in accordance with embodiments of the present invention.

DETAILED DESCRIPTION

Aspects of the present invention are generally directed to a system for fitting a hearing prosthesis to a recipient. The system uses real-time objective assessment of the recipient's hearing loss to automatically adjust operation of the hearing prosthesis. In embodiments of the present invention, the fitting system mechanically and/or acoustically stimulates the recipient's inner ear based on an input signal. The recipient's neural responses to the stimulation are detected and assessed. This assessment is used as a basis for adjustment of the operation of the hearing prosthesis.

In certain embodiments, the operation of the hearing prosthesis is adjusted so that stimulation is audible and comfortable for the recipient, referred to herein as providing optimal loudness restoration. The hearing prosthesis may also be adjusted such that input signals across a desired frequency range are perceived by the recipient with equal loudness. Similarly, the hearing prosthesis operation may be adjusted to provide enhanced speech perception of the input signals.

Because the fitting process is based on the objective detection of the recipient's neural responses, the recipient's subjective feedback generally is not required. Therefore, the unreliable and time consuming interactive communication between an audiologist and the recipient to fit the hearing prosthesis to the recipient is unnecessary.

Figure 1A:
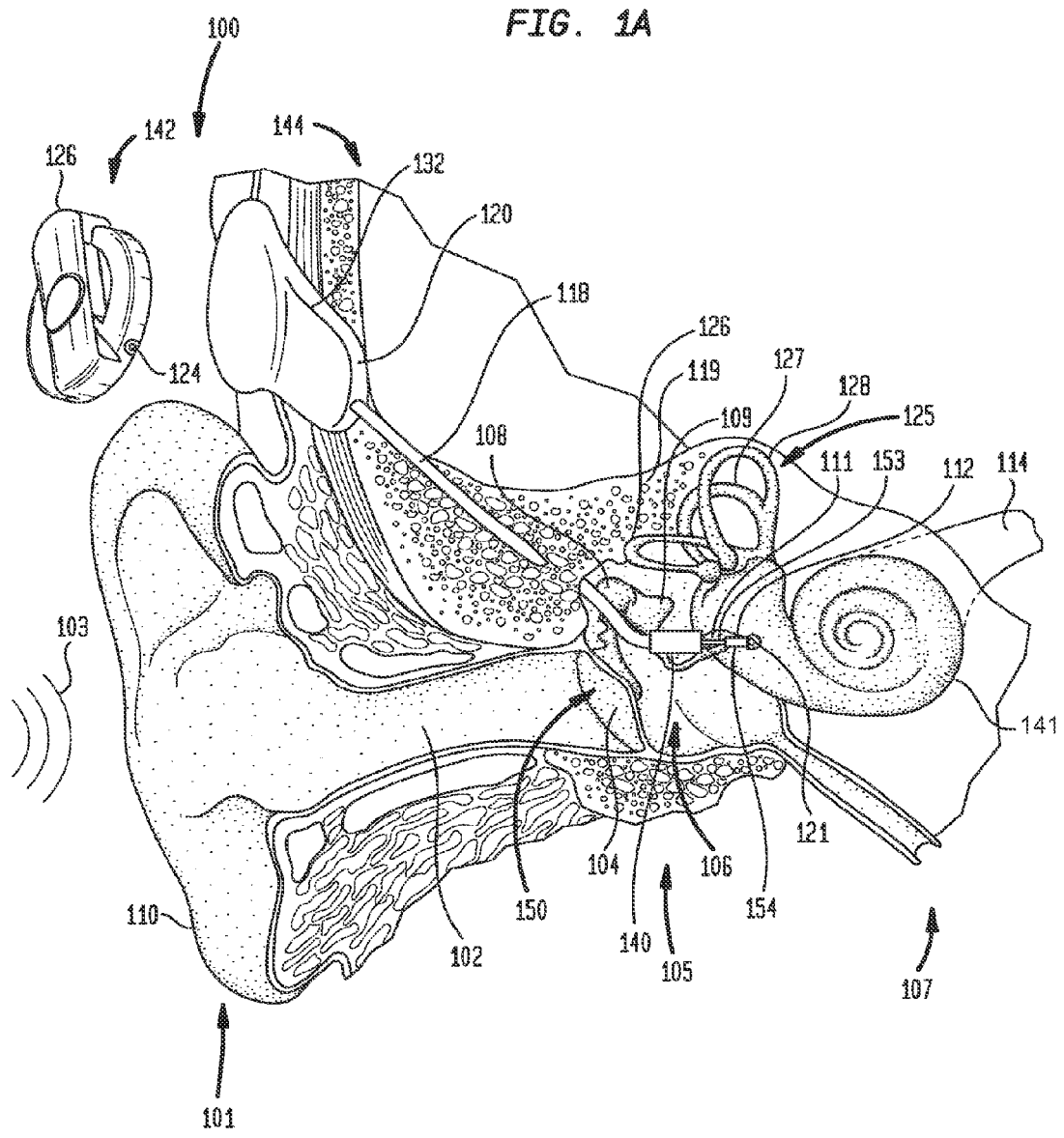
FIG. 1A is a perspective view of a hearing prosthesis in which embodiments of the present invention may be implemented.

FIG. 1A is perspective view of a mechanical stimulator 100 in which a fitting system in accordance with embodiments of the present invention may be implemented. Mechanical stimulator 100 is shown implanted in a recipient having an outer ear 101, a middle ear 105 and an inner ear 107. Components of outer ear 101, middle ear 105 and inner ear 107 are described below, followed by a description of mechanical stimulator 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound. Further details of cochlea 140 are described below with reference to FIGS. 1B and 1C.

As shown in FIG. 1A are semicircular canals 125. Semicircular canals 125 are three half-circular, interconnected tubes located adjacent cochlea 140. The three canals are the horizontal semicircular canal 126, the posterior semicircular canal 127, and the superior semicircular canal 128. The canals 126, 127 and 128 are aligned approximately orthogonally to one another. Specifically, horizontal canal 126 is aligned roughly horizontally in the head, while the superior 128 and posterior canals 127 are aligned roughly at a 45 degree angle to a vertical through the center of the individual's head.

Each canal is filled with a fluid called endolymph and contains hair cells (not shown) whose ends are embedded in a gelatinous structure called the cupula (also not shown). When the recipient's skull twists, the endolymph is forced into different sections of canals 125. The hair cells detect when the endolymph passes thereby, and an indication signal is then sent to the recipient's brain. Thus, using the hair cells, horizontal canal 126 detects horizontal head movements, while the superior 128 and posterior 127 canals detect vertical head movements.

As noted, FIG. 1A illustrates mechanical stimulator 100 having components implanted in a recipient. In the illustrative embodiment, mechanical stimulator 100, sometimes referred to as direct mechanical stimulator herein, is a hearing prosthesis which simulates natural hearing by directly generating mechanical motion of the fluid within a recipient's cochlear, thereby activating cochlear hair cells and evoking a hearing percept. Direct mechanical stimulator 100 comprises an external component 142 which is directly or indirectly attached to the body of the recipient, and an internal component 144 which is temporarily or permanently implanted in the recipient. External component 142 comprises one or more sound input elements, such as microphones 124, a sound processing unit 126, a power source (not shown), and an external transmitter unit (also not shown). The external transmitter unit provides power and stimulation data to internal component 144.

Internal component 144 comprises an internal receiver unit 132, a stimulator unit 120, and a stimulation arrangement 150. Internal receiver unit 132 comprises an internal coil (not shown), and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives the power and stimulation data from the external transmitter.

In the illustrative embodiment, stimulation arrangement 150 is implanted in middle ear 105. Stimulation arrangement 150 comprises an actuator 140, a stapes prosthesis 154 and a coupling element 153 connecting the actuator to the stapes prosthesis. Actuator 140 is connected to stimulator unit 120 by cable 118 extending through mastoid bone 119. As described in greater detail below with reference to FIG. 5, in this embodiment stimulation arrangement 150 is implanted and/or configured such that a portion of stapes prosthesis 254 abuts round window 121.

In operation, a sound signal is received by one or more microphones 124, processed by sound processing unit 126, and transmitted as encoded data signals to internal receiver 132. Based on these received signals, stimulator 1220 generates electrical signals which cause actuation of actuator 140. This actuation is transferred to stapes prosthesis 154 such that a wave of fluid motion is generated in the perilymph in scala tympani 138 (FIG. 1B). Such fluid motion, in turn, activates the hair cells of the organ of Corti 150 (FIG. 1C). Activation of the hair cells causes appropriate nerve impulses to be generated and transferred through the spiral ganglion cells (not shown) and auditory nerve 114 to the brain (also not shown) where they are perceived as sound.

As noted above, FIGS. 1B and 1C illustrate further details of cochlea 140. FIG. 1B is a perspective view of cochlea 140 partially cut-away to display the canals and nerve fibers of the cochlea. FIG. 1C is a cross-sectional view of one turn of the canals of cochlea 140. Referring to FIG. 1B, cochlea 140 is a conical spiral structure comprising three parallel fluid-filled canals or ducts, collectively and generally referred to herein as canals 132. Canals 132 comprise the tympanic canal 138, also referred to as the scala tympani 138, the vestibular canal 134, also referred to as the scala vestibuli 134, and the median canal 136, also referred to as the cochlear duct 136. Cochlea 140 has a conical shaped central axis, the modiolus 154, that forms the inner wall of scala vestibuli 134 and scala tympani 138. The base of scala vestibuli 134 comprises oval window 112 (FIG. 1A), while the base of scala tympani 138 terminates in round window 121 (FIG. 1A). Tympanic and vestibular canals 138, 134 transmit pressure waves received at oval window 112, while medial canal 136 contains the organ of Corti 150 which detects pressure impulses and responds with electrical impulses which travel along auditory nerve 114 to the brain (not shown).

Cochlea 140 spirals about modiolus 154 several times and terminates at cochlea apex 146. Modiolus 154 is largest near its base where it corresponds to first turn 151 of cochlea 140. The size of modiolus 154 decreases in the regions corresponding to medial 152 and apical turns 156 of cochlea 140.

Referring now to FIG. 1C, separating canals 132 of cochlear 140 are various membranes and other tissue. The Ossicous spiral lamina 182 projects from modiolus 154 to separate scala vestibuli 134 from scala tympani 138. Toward lateral side 172 of scala tympani 138, a basilar membrane 158 separates scala tympani 138 from median canal 136. Similarly, toward lateral side 172 of scala vestibuli 134, a vestibular membrane 166, also referred to as the Reissner's membrane 166, separates scala vestibuli 134 from median canal 136.

Portions of cochlea 140 are encased in a bony capsule 170. Bony capsule 170 resides on lateral side 172 (the right side as drawn in FIG. 1C), of cochlea 140. Spiral ganglion cells 180 reside on the opposing medial side 174 (the left side as drawn in FIG. 1C) of cochlea 140. A spiral ligament membrane 164 is located between lateral side 172 of spiral tympani 138 and bony capsule 170, and between lateral side 172 of median canal 136 and bony capsule 170. Spiral ligament 164 also typically extends around at least a portion of lateral side 172 of scala vestibuli 134.

The fluid in tympanic and vestibular canals 138, 134, referred to as perilymph, has different properties than that of the fluid which fills median canal 136 and which surrounds organ of Corti 150, referred to as endolymph. Sound entering auricle 110 causes pressure changes in cochlea 140 to travel through the fluid-filled tympanic and vestibular canals 138, 134. As noted, organ of Corti 150 is situated on basilar membrane 158 in median canal 136. It contains rows of 16,000-20,000 hair cells (not shown) which protrude from its surface. Above them is the tectoral membrane 162 which moves in response to pressure variations in the fluid-filled tympanic and vestibular canals 138, 134. The changes in pressure caused by the traveling wave(s) in the tympanic and vestibular canals 138, 134 cause small relative movements of the layers of membrane 162, which are sufficient to cause the hair cells to send a voltage pulse or action potential down the associated nerve fiber 178. Nerve fibers 178, embedded within spiral lamina 182, connect the hair cells with the spiral ganglion cells 180 which form auditory nerve 114. Auditory nerve 114 relays the impulses to the auditory areas of the brain (not shown) for processing.

FIG. 2A is a functional block diagram of a mechanical stimulator 200 configured to implement embodiments of the present invention. As shown, mechanical stimulator 200 comprises an external component 242 and an internal component 244. External component 242 comprises one or more sound input elements 224, a sound processing unit 226 and a transmitter unit 246. Sound processing unit 226 further comprises a processing module 210, control electronics 254, a user interface 251 and a power source 208.

Sound input element 224 receives a sound 203 and outputs an electrical signal 261 representing the sound to processing module 210 in sound processing unit 226. Processing module 210 generates encoded signals 262 which are provided to transmitter unit 646. As should be appreciated, processing module 210 generates encoded signals 262 by using one or more of a plurality of techniques to selectively process, amplify and/or filter electrical signal 261.

Transmitter unit 246 is configured to transmit encoded data signals 262 to internal component 244. In certain embodiments, transmitter unit 246 comprises an external coil which forms part of a bi-directional data communication link 247 with components of internal component 244. Link 247 may comprise, for example, a radio frequency (RF) link 247.

Internal component 244 comprises an internal receiver unit 248 and a stimulator unit 220 which are hermetically sealed within a biocompatible housing, sometimes collectively referred to as a stimulator/receiver unit 249. Internal receiver unit 248 comprises an internal coil which forms a component of RF link 247 and which is used to receive power and encoded signals from the external coil in external transmitter unit 246. The encoded signals 262 received by internal receiver unit 248 are provided to stimulator unit 220. Based on the received signals, stimulator unit 220 is configured to deliver electrical drive signals 264 to an actuator 240 which comprises part of a stimulation arrangement. Based on drive signals 264, actuator 240 is configured to generate volumetric displacement of the recipient's inner ear fluid. In other words, actuator 240 is coupled to one or more components of the recipient's middle or inner ears so as cause mechanical displacement of the inner ear fluid. This fluid displacement generates a wave which travels along the recipient's basilar membrane, thereby evoking a hearing percept of sound 203. As discussed in greater detail below with reference to FIGS. 4 and 5, actuator 240 may be coupled to various middle or inner ear components in order to provide the vibration to the inner ear fluid.

Internal component further comprises electrical contacts 252 and a sense amplifier 280. Details of contacts 252 and sense amplifier 280 are provided below with reference to FIG. 2B.

As shown in FIG. 2A. sound processing unit 226 further comprises a user interface 251 and control electronics 254. These components may function together to permit a recipient or other user of mechanical stimulator 200 to control or adjust the operation of the stimulator. For example, in certain embodiments of the present invention, based on inputs received by a user interface 251, control electronics 254 may provide instructions to, or request information from, other components of mechanical stimulator 200. User interface 251 may comprise one or one or buttons or inputs which allow the recipient to adjust the volume, alter the speech processing strategies, power on/off the device, etc.

Operation of mechanical stimulator 200 may be based on previous programming, such as default or initially programming provided by an audiologist, clinician, surgeon or other medical specialist (collectively and generally referred to as audiologist herein.) As used herein, programming refers to the settings or parameters used by the stimulator to receive and process a sound signal and to stimulate the recipient based on the sound signal.

Figure 2B:
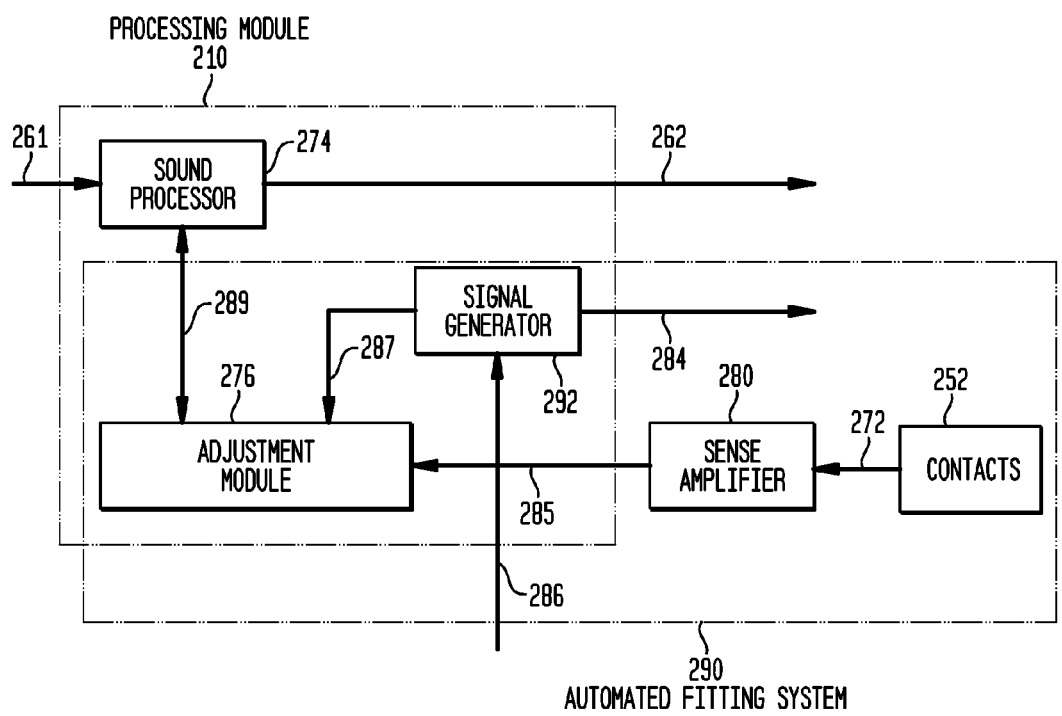
FIG. 2B is a functional block diagram illustrating the components of a processing module of the hearing prosthesis of FIG. 2A, in accordance with embodiments of the present invention.

Based on the previous programming, mechanical stimulator 200 receives a sound signal and stimulates the recipient so as to evoke a hearing percept of the sound signal. As shown in FIG. 2B, mechanical stimulator 200 includes an automated fitting system 290 which uses real-time objective assessment of the recipient's hearing loss to automatically adjust the operation of the stimulator by, for example, adjusting the previous programming. More specifically, as detailed below, automated fitting system 290 mechanically and/or acoustically stimulates the recipient's inner ear based on an input signal. The recipient's neural responses to the stimulation are detected and assessed. This assessment is used as a basis for adjustment of the operation of mechanical stimulator 200.

Automated fitting system 290 may be configured to adjust the operation of mechanical stimulator 290 so that stimulation is audible by and comfortable for the recipient. Automated fitting system 290 may further adjust the operation of mechanical stimulator 200 such that input signals across a desired frequency range are perceived by the recipient with equal loudness. Similarly, automated fitting system 290 may further adjust the operation of stimulator 200 to provide enhanced speech perception of the received sound signals.

Because automated fitting system 290 uses the objective detection of the recipient's neural responses, the recipient's subjective feedback generally is not required. Therefore, the unreliable and time consuming interactive communication between an audiologist and the recipient that is generally required to fit the hearing prosthesis to the recipient is unnecessary.

FIG. 2B is a functional block diagram illustrating components of processing module 210 of FIG. 2A in which components of automated fitting system 290 may be implemented. Processing module 210 comprises a sound processor 274 which is configured to convert electrical signal 261 representing received sound 203 (FIG. 2A) into encoded data signals 262. These encoded signals are then transmitted to internal component 244 (FIG. 2A) for use in evoking a hearing percept of sound 203. Sound processor 274 generates encoded signals 262 by using one or more of a plurality of techniques to selectively process, amplify and/or filter electrical signal 261. As would be appreciated, processing module 210, or components thereof, may comprise a digital signal processor.

Automated fitting system 290 comprises a signal generator 292, actuator 240 (FIG. 2A), electrical contacts 252, a sense amplifier 280 and an adjustment module 276. As shown, automated fitting system 290 is configured to automatically adjust the processing of signal 261 by sound processor 274.

In operation, signal generator 292 generates electrical signals 284 representing a broad range of frequencies that are audible by an individual with normal or undamaged hearing, referred to as audible frequencies. Signal generator 292 is configured to generate electrical signals 284 in accordance with the current programming and processing settings of sound processor 274. Audible frequencies generally range from approximately 20 HZ to approximately 20 kHz. As such, signal generator 292 may, for example, generate electrical signals 284 representing signals having a frequency of approximately 100 Hz to approximately 12 kHz, though other ranges may also be used.

Signals 284 are used to generate a volumetric displacement of the recipient's inner fluid. In the illustrative embodiments of FIGS. 2A and 2B, the volumetric displacement is provided by actuator 240. Signals 284 are provided to stimulator unit 220 (FIG. 2A) via RF link 247. Stimulator 220 then generates drive signals which cause actuator 140 to cause inner ear fluid displacement corresponding to the desired frequencies. The inner ear fluid displacement generates a traveling wave on the recipient's basilar membrane due to pressure differences between the scala vestibuli 134 (FIG. 1B) and scala tympani 138 (FIG. 1B). The traveling wave on the basilar membrane excites the cochlear hair cells, thereby evoking a hearing percept.

Concurrently with the generation of the inner ear fluid displacement, automated fitting system 290 is configured to detect or record the response of the recipient's auditory nerves to the generated fluid displacement. The detected neural responses provide an objective measurement of the response of the various nerve cells to the mechanical stimulation. Various methods and systems may be used to detect the recipient's neural responses. As described in greater detail below with reference to FIG. 6, the exemplary arrangement of FIG. 2B uses electrical contacts and a sense amplifier to detect the neural responses.

In the embodiments of FIG. 2B, sense amplifier 280 outputs sensed output signals 285 representing the detected neural responses. Sensed output signals 285 are provided to adjustment module 276 which implements, in real time, a set of algorithms which assess the detected neural responses, and which adjust the operation of stimulator 200 based on the assessment. For example, in embodiments discussed in greater detail below with reference to FIG. 7, the algorithms implemented by adjustment module 276 use output signals 285 to compare the detected neural responses to, for example, target neural responses and/or predicted neural responses.

As noted above, in the embodiment of FIG. 2B adjustment module 276 is configured to adjust the operations of sound processor 274 via signal line 289. This may include adjusting any of the operations performed by the stimulator to filter, process and/or amplify electrical signal 261 so that equal loudness and loudness restoration are optimized across a desired number of audible frequencies.

FIGS. 2A and 2B have been discussed herein with reference to a mechanical actuator coupled to the recipient's middle or inner ear to provide displacement of the inner ear fluid. It should be appreciated that in embodiments of the present invention, acoustical stimulation, rather than mechanical stimulation, is used to generate the desired displacement of the inner ear fluid. In these embodiments, signals 284 from signal generator are provided to, for example, an audio output device, such as a loudspeaker driven by an audio amplifier configured to provide programmable gain across the audible frequencies. An audio signal output by the loudspeaker is provided to the cochlea via, for example, the recipient's middle ear to generate the desired fluid displacement and resulting hearing percept.

In the embodiment of FIG. 2B, sense amplifier 280 is shown separate from processing module 210. As shown in FIG. 2A, sense amplifier 280 comprises a component of internal component 244 and, as such, output signals 285 are transmitted via RF link 247 to adjustment module 276.

For ease of illustration, the embodiments of FIG. 2B have been illustrated with an automated fitting system 290 which comprises a signal generator 292 which is separate from sound processor 274. It should be appreciated that in certain embodiments, sound processor 274 may function as the signal generator and would generate electrical signals 284 representing a broad range of audible frequencies. Therefore, in such embodiments separate signal generator 292 would be unnecessary.

In certain embodiments, the automated fitting system 290 periodically assesses the recipient's neural responses to an input signal, and adjusts the stimulator operations as needed. In other embodiments, the automated fitting system 290 operates upon the occurrence of predetermined events, such as start-up of stimulator 200, entry of manual inputs 286 by a recipient or audiologist, etc. In other embodiments, automated fitting system 290 continually monitors a recipient's neural responses to stimulation signals.

In one embodiment, a set of therapeutic or safety guidelines are programmed into automated fitting system 290 which limit the adjustment of the stimulator operations. Specifically, these guidelines prevent adjustment of the operation of stimulator 200 that would result in stimulation damaging to the recipient's hearing.

For ease of illustration, automated fitting system 290 has been described above as integrated into mechanical stimulator 200. It should be appreciated that an automated fitting system in accordance with embodiments of the present invention may be integrated into any hearing prosthesis which delivers stimulation to a recipient's outer, middle or inner ear, including acoustic hearing aids, direct or indirect mechanical stimulators, cochlear implants, bone conduction devices, etc. It should also be appreciated that an automated fitting system in accordance may be implemented separate from a hearing prosthesis. For example, an automated fitting system of the present invention may comprise a stand-alone unit.

Although the embodiments of FIGS. 2A and 2B have been described with reference to a mechanical stimulator 200 having an external component, it should be appreciated that in alternative embodiments mechanical stimulator 200 is a totally implantable device. In such embodiments, sound processing unit 226 is implanted in a recipient in the mastoid bone.

Figure 3:
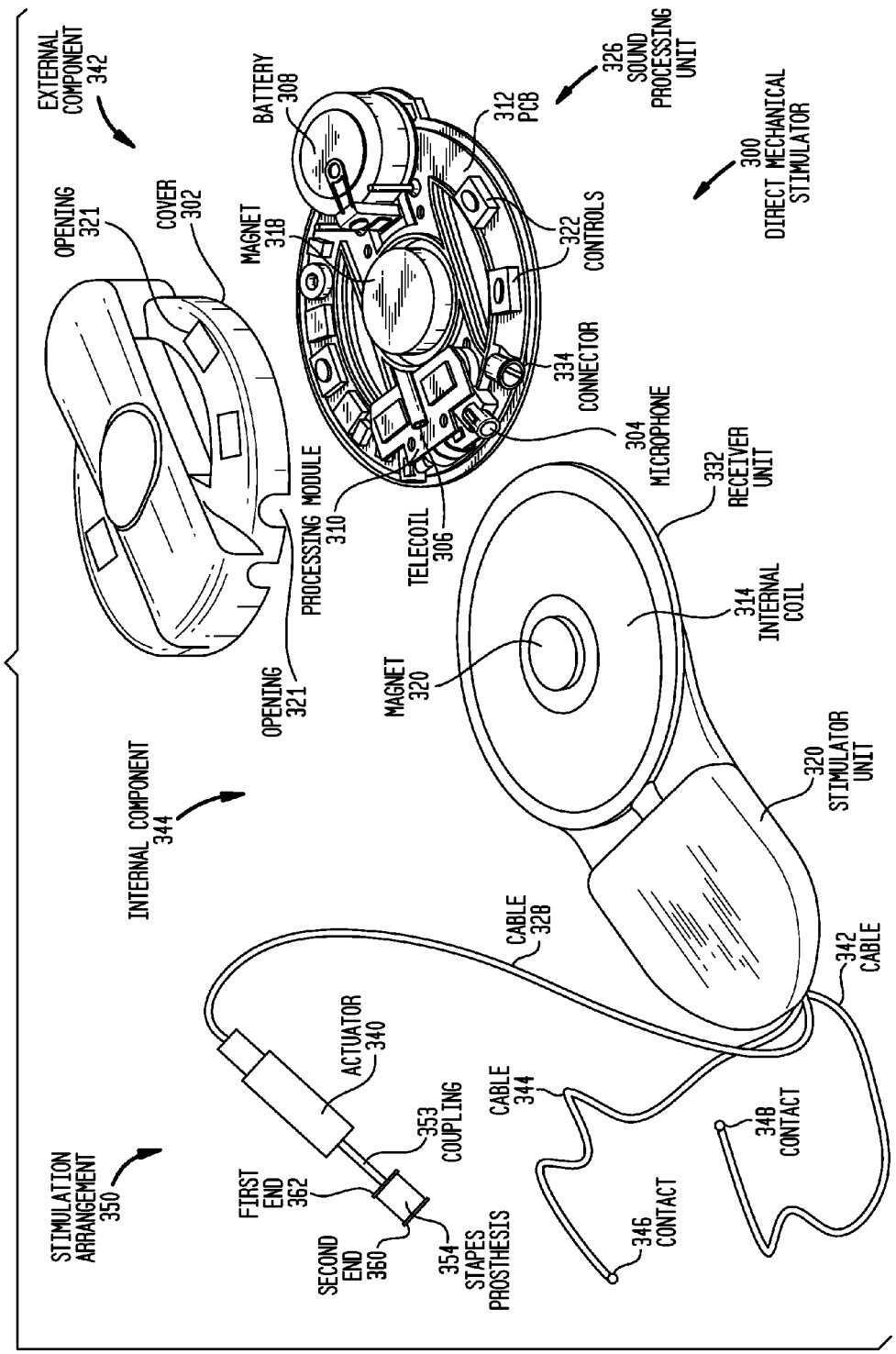
FIG. 3 is a partially exploded top view of a mechanical stimulator, in accordance with embodiments of the present invention.

FIG. 3 is a partially exploded top view of a direct mechanical stimulator 300 in which embodiments of the present invention may be advantageously implemented. Direct mechanical stimulator 300 comprises an external component 342 and an internal component 344. External component 342 includes a sound processing unit 326 having disposed therein or thereon one or more sound input elements configured to receive an input sound signal. In the illustrative embodiment of FIG. 3, sound processing unit 326 has microphones 324 disposed therein to receive an acoustic sound signal. Sound processing unit 326 further comprises an electrical connector 334. Electrical connector 334 is configured to connect direct mechanical stimulator 300 to external equipment, and to receive an electrical signal, such as an electrical sound signal, directly there from. Electrical connector 334 provides the ability to connect direct mechanical stimulator 300 to, for example, FM hearing systems, MP3 players, televisions, mobile phones, etc. Direct mechanical stimulator 300 further includes a sound input element in the form of a telecoil 306. Telecoil 306 provides the ability to receive input sound signals from, for example, a telephone or other similar device.

Sound processing unit 326 further includes a processing module 310 which processes sound signals received by the sound input elements. Sound processing module 310 generates encoded data signals based on the received sound signals. Similar to the embodiments discussed above with reference to FIGS. 2A and 2B, processing module 310 further includes components of an automated fitting system.

To provide control over the sound processing and other functionality of direct mechanical stimulator 300, sound processing unit 326 includes one or more user controls 322. Integrated in sound processing unit 326 is a battery 308 which provides power to the other components of direct mechanical stimulator 300. Sound processing unit 326 further includes a printed circuit board (PCB) 312 to mechanically support and electrically connect the above and other functional components. Disposed on the exterior surface of sound processing unit 326 is an external transmitter unit (not shown).

For ease of illustration, sound processing unit 326 has been shown with cover 302 removed. Cover 302 further has one or more openings 321 therein which receive user controls 322, microphones 304 and connector 334. Cover 302 is configured to seal sound processing unit 326 so as to prevent the ingress of water, dust and other debris, particularly through openings 321.

Internal component 344 comprises an internal receiver unit 332, a stimulator unit 320, and a stimulation arrangement 350. As shown, receiver unit 232 comprises an internal coil 314, and preferably, a magnet 320 fixed relative to the internal coil. The external transmitter unit in external component 344 transmits electrical signals (i.e., power and stimulation data) to internal coil 314 via a radio frequency (RF) link. Signals received at internal coil 314 may be provided to stimulator unit 320. As would be appreciated, internal receiver unit 332 and stimulator unit 320 would be hermetically sealed within a biocompatible housing. This housing has been omitted from FIG. 3 for ease of illustration.

Connected to stimulator unit 320 via a cable 328 is a stimulation arrangement 350. Stimulation arrangement 350 comprises an actuator 340, a stapes prosthesis 354 and a coupling element 353. A second end of stapes prosthesis 354 is configured to be positioned abutting an opening in a recipient's inner ear, while a first end of stapes prosthesis 354 is connected to actuator 340 via a coupling 353. As described below with reference to FIGS. 4 and 5, actuation of actuator 340 vibrates stapes prosthesis 354. The vibration of stapes prosthesis 354 generates waves of fluid motion of the cochlear fluid, thereby generating a wave on the recipient's basilar membrane that activates the hair cells of the organ of Corti 150 (FIG. 1C). Activation of the hair cells causes appropriate nerve impulses to be generated and transferred through the spiral ganglion cells (not shown) and auditory nerve 114 to the brain (also not shown) where they are perceived as sound.

Internal component 344 further comprises electrical contacts 346 and 348 which, as described below with reference to FIG. 6, are used to detect the neural responses to the mechanical stimulation provided by stimulation arrangement 350. In the exemplary embodiment of FIG. 3, contacts 346 and 348 are coupled to a sense amplifier (not shown) via cables 344, 342, respectively.

FIG. 3 has been illustrated herein with reference to a stimulation arrangement configured to mechanically stimulate the recipient's inner ear. It should be appreciated that the illustrated embodiments are merely exemplary and that in alternative embodiments the stimulation arrangement may comprise, for example, an audio output device configured to generate an amplified audio signal across a desired audible frequency range. In these embodiments, the audio signal is delivered to, for example, the recipient's middle ear to generate displacement of the inner ear fluid.

Figure 4:
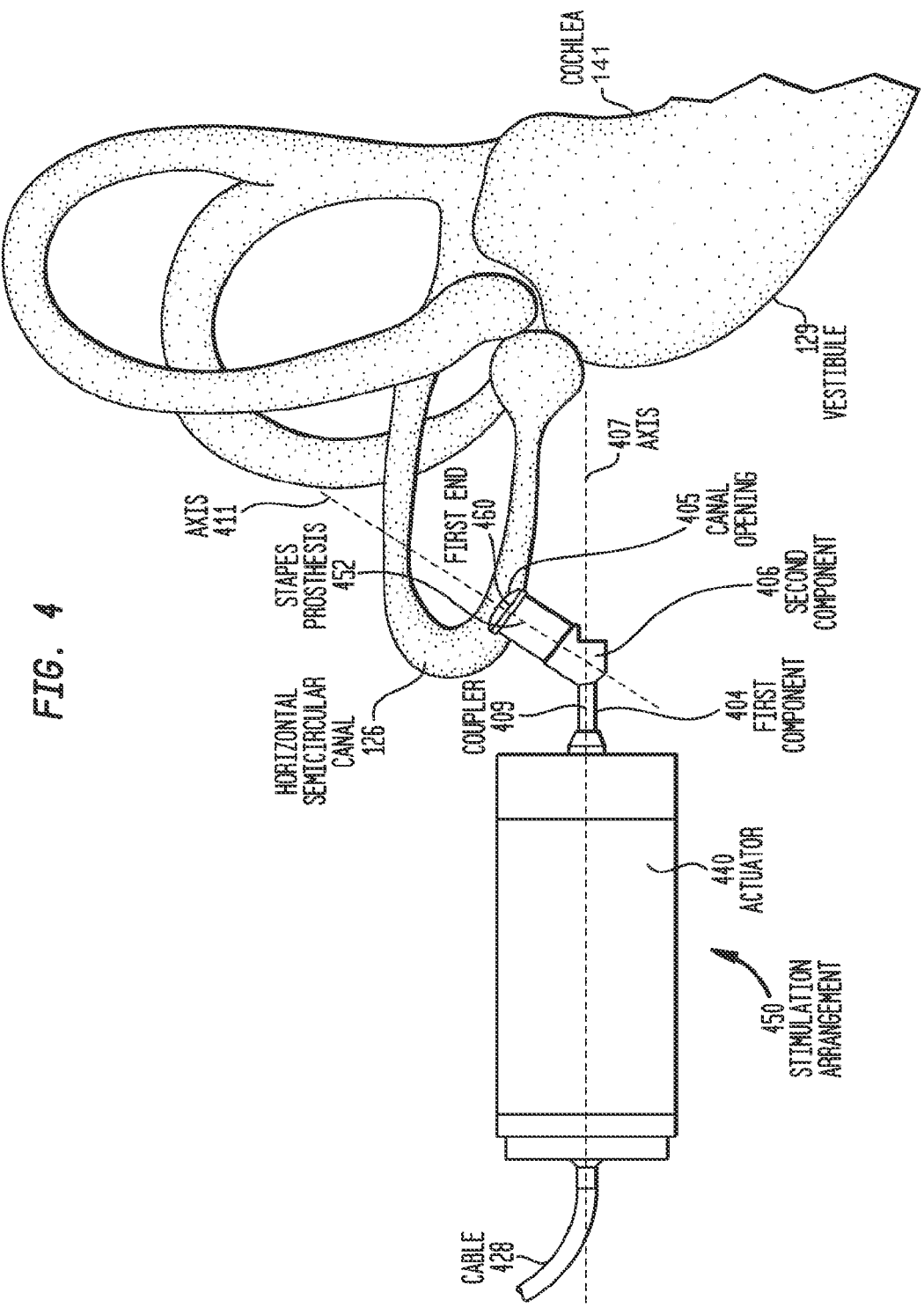
FIG. 4 is a perspective view of a mechanical stimulation arrangement, in accordance with embodiments of the present invention.

FIG. 4 illustrates a stimulation arrangement 450 which may be used in accordance with embodiments of the present invention. In the illustrative embodiment of FIG. 4, stimulation arrangement 450 is configured to generate fluid motion of the endolymph contained in a recipient's semicircular canal 126. Because vestibule 129 provides fluid communication between the semicircular canal 126 and the median canal 136 (FIG. 1B), the wave of fluid motion continues into median canal 136, thereby activating the hair cells of the organ of Corti 150 (FIG. 1C). Activation of the hair cells causes appropriate nerve impulses to be generated and transferred through the spiral ganglion cells (FIG. 1C) and auditory nerve (FIG. 1A) to the recipient's brain where they are perceived as sound.

As detailed above, stimulation arrangement 450 may further comprise part of an automated fitting system. In such embodiments, stimulation arrangement 450 is utilized to generate the displacement of recipient's inner ear fluid in response to signals provided by a signal generator. The fluid displacement evokes a hearing percept, and the resulting neural responses are detected and used as basis for adjustment.

In the illustrative embodiment, stimulation arrangement 450 comprises an actuator 440 coupled to a stimulator unit (not shown) by one or more cables 428. Actuator 440 may be positioned and secured to the recipient by a fixation system. Stimulation arrangement 450 further comprises a stapes prosthesis 452. In the illustrative embodiment, stapes prosthesis 452 is a substantially cylindrical member having a first end 460 abutting an opening 405 in the recipient's horizontal semicircular canal 126.

Connecting actuator 440 and stapes prosthesis 452 is a coupler 409. Coupler 409 comprises a first elongate component 404 extending longitudinally from actuator 440. Disposed at the distal portion of first component 404 is a second component 406. Second component 406 is oriented such that the component extends away first component 404 at an angle and connects to stapes prosthesis 452. In other words, an axis 411 extending through the center of second component 406 along the direction of orientation is at an angle from the longitudinal axis 407 of first component 404. In certain embodiments, second component 406 is oriented such that axis 411 is positioned at an angle of approximately 125 degrees from longitudinal axis 407.

As would be appreciated, there is limited space within a recipient's skull in which stimulation arrangement 450 may be implanted particularly if the recipient's middle ear is left undisturbed. As such, due to these size constraints the orientation of second component 406 relative to first component 404 may facilitate the proper or desired positioning of stapes prosthesis 452 to optimally mechanically stimulate the recipient. To implant stimulation arrangement 450 illustrated in FIG. 4, a surgeon may drill or form a passageway in the mastoid of the skull. This passageway is preferably constructed and arranged such that it provides direct access to the cochlea. In this embodiment, the surgeon then drills or forms an opening in semicircular canal 126 of the recipient. Stimulation arrangement 450 may be implanted in the formed passageway and/or the recipient's middle ear cavity, and the arrangement is configured so that stapes prosthesis 452 is positioned abutting the opening in the semicircular canal 126. In the illustrative embodiment of FIG. 4, this opening is created in horizontal semicircular canal 126. It would be appreciated that an opening created in posterior semicircular canal 127 (FIG. 1A) or superior semicircular canal 128 (FIG. 1A) may also be used.

Figure 5:
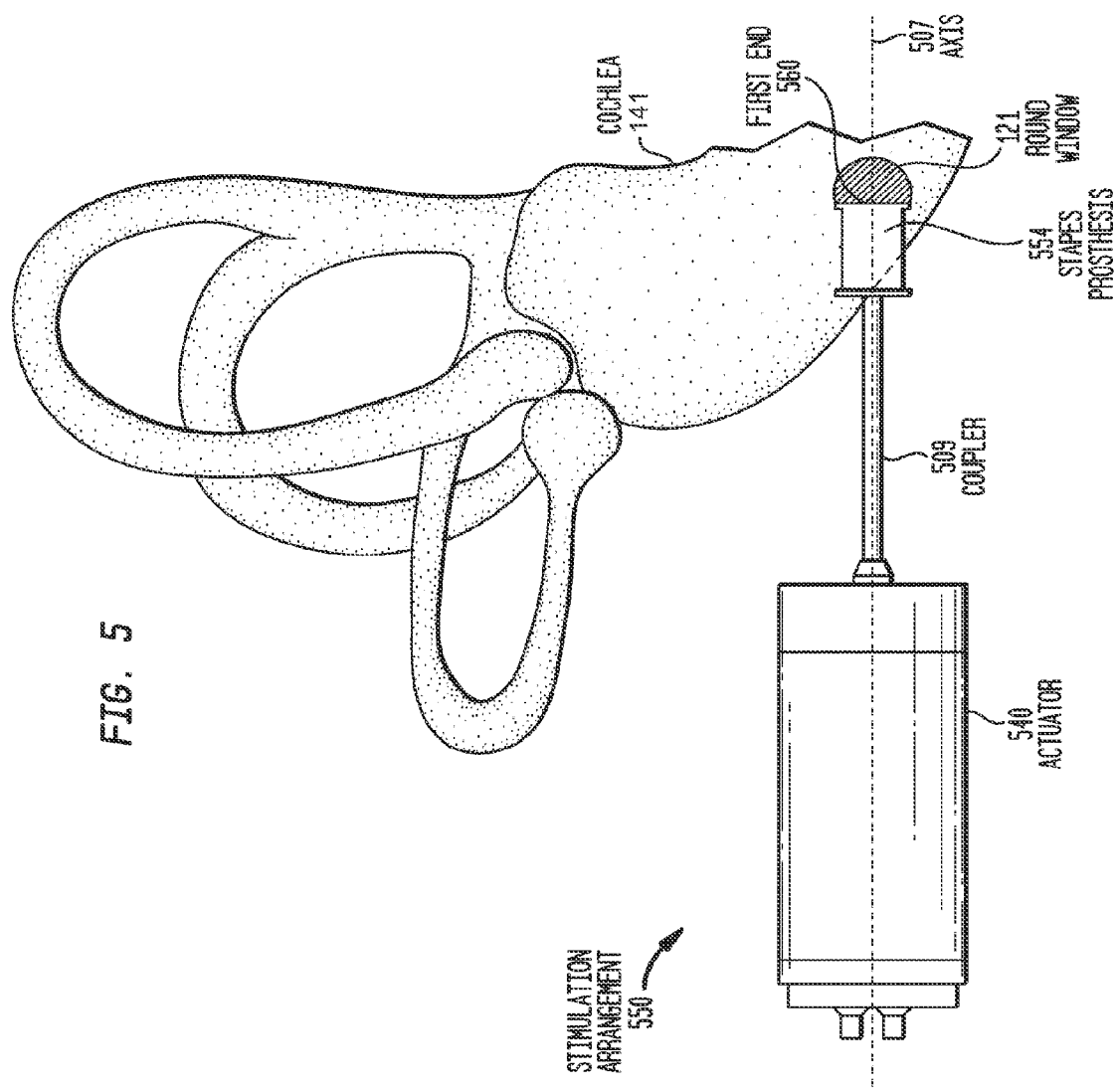
FIG. 5 is a perspective view of a mechanical stimulation arrangement, in accordance with embodiments of the present invention.

FIG. 5 illustrates a stimulation arrangement 550 in accordance with embodiments of the present invention. In the illustrative embodiment of FIG. 5, stimulation arrangement 550 is configured to generate fluid motion of the perilymph contained in a recipient's scala tympani 138 (FIG. 1B). As discussed above, fluid motion of the perilymph generates a traveling wave on the recipient's basilar membrane that activates the hair cells of the organ of Corti 150 (FIG. 1C). Activation of the hair cells causes appropriate nerve impulses to be generated and transferred through the spiral ganglion cells (FIG. 1C) and auditory nerve (FIG. 1A) to the recipient's brain where they are perceived as sound.

As detailed above, stimulation arrangement 550 may further comprise part of an automated fitting system. In such embodiments, stimulation arrangement 550 is utilized to generate the displacement of recipient's inner ear fluid in response to signals provided by a signal generator. The fluid displacement evokes a hearing percept, and the resulting neural responses are detected and used as basis for adjustment.

In the illustrative embodiment, stimulation arrangement 550 comprises an actuator 540. Actuator 540 may be positioned and secured to the recipient by a fixation system. Details of an exemplary fixation system are provided below with reference to FIG. 7. Stimulation arrangement 550 further comprises a stapes prosthesis 554. As shown in FIG. 5C, stapes prosthesis 554 is a substantially cylindrical member having a first end 560 and a second end 514. As shown, first and second ends 560 and 514 have cross-sectional diameters which exceed the cross-sectional diameter of the remainder of prosthesis 554. Returning to FIG. 5, distal end 560 is configured to be positioned abutting the membrane of round window 121 in the recipient's cochlea.

Connecting actuator 540 and stapes prosthesis 554 is a coupler 509. Due to size constraints, there may be limited locations in which actuator 540 may be implanted within the recipient, particularly if the recipient's inner ear is to remain undisturbed. FIG. 5 illustrates embodiments in which actuator 540 is positioned substantially in line with round window 121. That is, actuator 540 is positioned along or parallel to an axis extending through the geometric center of round window 121. As such, in this exemplary configuration coupler 509 comprises an elongate rod extending longitudinally from actuator 540 along axis 507. The distal portion of rod 508 is connected to stapes prosthesis 554. In the illustrative embodiment of FIG. 5, stapes prosthesis 554 is aligned along, and is substantially symmetrical about axis 507. In other words, the surface of first end 560 is positioned orthogonal to axis 507.

FIG. 6 is a cross-sectional view of cochlea 141 illustrating one exemplary system for detecting a recipient's neural responses to mechanical and/or acoustical stimulation, referred to herein as neural response detection arrangement 600. As noted above with reference to FIG. 2B, detection arrangement 600 comprises part of an automated fitting system.

As shown in FIG. 6, detection arrangement 600 comprises two electrical contacts 646, 648 positioned on cochlea 141.

Contacts 646, 648 are electrically connected to sense amplifier 602 and, in this embodiment, form a dipole across cochlea 141. When the automated fitting system mechanically and/or acoustically stimulates cochlea 141, contacts 646, 648 detect the recipient's neural response to the stimulation. That is, contacts 646, 648 detect the response of the recipient's auditory nerves to the generated fluid displacement. Contacts 646, 648 may be positioned at any suitable location on or near cochlea 141. For example, in certain embodiments, contacts 646, 648 may be positioned on the bone adjacent cochlea 141 or on the semicircular canals 125.

The signals detected by contacts 646, 648 are provided to sense amplifier 602. In embodiments in which acoustical stimulation is generating using a signal source, such as a loudspeaker, sense amplifier 602 has an input bandwidth which is equal to the output bandwidth of the signal source.

It should be appreciated that the arrangement of FIG. 6 for detecting the recipient's neural responses is illustrative, and various other systems or arrangements for detecting a neural response are within the scope of the present invention. For example, it should be appreciated that in alternative embodiments more or less contacts may be used to detect the neural response.

Figure 7A:
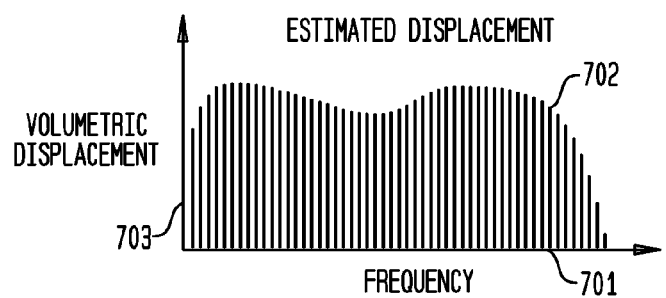
FIG. 7A is a graph illustrating the estimated volumetric displacement of inner ear fluid at various frequencies following resulting from stimulation in accordance with an input signal.

As discussed above, in embodiments of the present invention, the recipient's inner ear is mechanically or acoustically stimulated across a broad range of audible frequency. FIG. 7A is a graph 702 illustrating the predicted or estimated volumetric displacement of a recipient's inner car fluid in response to an input signal. More specifically, FIG. 7A illustrates the volumetric displacement which is estimated to physically occur when the recipient's inner ear is mechanically or acoustically stimulated in accordance with the input signal. Axis 701 illustrates the frequencies at which the recipient is stimulated, while axis 703 illustrates the estimated displacement at each frequency.

The volumetric displacement at each frequency may be estimated using a variety of factors. For example, the estimated displacement is based on a specific recipient's characteristics, the characteristics of the general population, and/or the characteristics of a specific group of the general population.

Figure 7B:
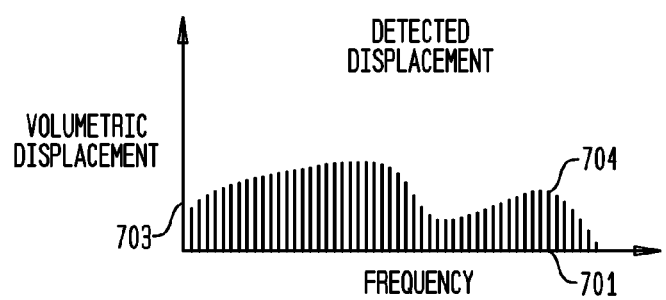
FIG. 7B is a graph illustrating detected volumetric displacements of inner fluid at various frequencies following application of stimulation in accordance with the input signal.

FIG. 7B is a graph 704 illustrating an exemplary detected volumetric displacements of inner fluid at various frequencies following the stimulation in accordance with the input signal of FIG. 7A. Specifically, FIG. 7B illustrates the displacement which is perceived by the recipient, regardless of how much displacement physically occurs. Due to the recipient's hearing loss, the detected displacement is less than the displacement which physically occurs (shown above in FIG, 7A). It should be appreciated that because the detected displacement is based on the individual recipient's hearing loss, other detected displacements are possible for different recipients. It should be appreciated that the detected displacement may be determined based on the recipient's above described detected neural responses.

Figure 7C:
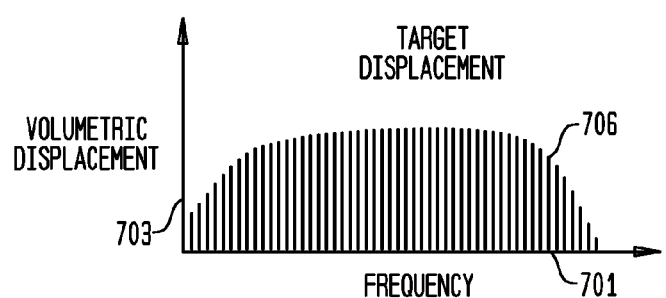
FIG. 7C is a graph illustrating the target volumetric displacement of inner fluid at various frequencies following application of the input signal.

FIG. 7C is a graph 704 illustrating the target or desired detected volumetric displacement of inner fluid at various frequencies following the input of FIG. 7C. This desired displacement provides the recipient with an optimal degree of loudness across the audible frequencies, as well as provides optimal loudness restoration. The desired displacement may be achieved by appropriately adjusting how the mechanical and/or acoustical stimulation is generated in the manner described above with reference to FIG. 2B.

As noted above, an automated fitting system in accordance with embodiments of the present invention is configured to assess the recipient's neural responses and to adjust the operation of a hearing prosthesis based on that assessment. In certain embodiments, the fitting system may make this assessment by using the detected neural responses to compare the sound perceived by the user to an estimated or predicted perception, represented by FIG. 7A. Adjustments to the hearing prosthesis operation would occur so that the sounds perceived by the recipient substantially match the estimated perception. In other embodiments, the fitting system may make the assessment by using the detected neural responses to compare the sound perceived by the user to a target perception, represented by FIG. 7C.

FIG. 8 illustrates a real-time method 800 which may be implemented by an automated fitting system to automatically fit a hearing prosthesis to a recipient, in accordance with embodiments of the present invention. At block 804, the automated fitting system mechanically and/or acoustically stimulates the recipient's inner ear using the hearing prosthesis. At block 806, the automated fitting system detects the recipient's neural responses to the mechanical and/or acoustical stimulation.

At block 810, the automated fitting system assesses the recipient's neural response. This assess may occur using a set of algorithms. At block 812, the programming of the hearing prosthesis is adjusted based on the assessment of the neural responses. In certain embodiments, the hearing prosthesis programming is adjusted to ensure that optimal loudness restoration across a range of audible frequencies. Similarly, the programming may also be adjusted to ensure equal loudness across a range of audible frequencies.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A system for fitting a hearing prosthesis to a recipient, comprising:

a stimulation arrangement that at least one of mechanically and acoustically stimulates the recipient to generate displacement of the fluid within the recipient's inner ear based on an input signal;

a neural response detection arrangement comprising at least first and second electrical contacts disposed on the outside of recipient's inner ear to detect a neural response of the recipient's auditory nerves to the displacement of the fluid within the recipient's inner ear; and a processor that executes a set of algorithms to assess the recipient's neural response in real-time and that adjusts operation of the hearing prosthesis based on the assessment of the neural response.

2. The system of claim 1, wherein the stimulation arrangement comprises:

an audio output device that generates an amplified audio signal representing the input signal.

3. The system of claim 1, wherein the stimulation arrangement comprises:

a stapes prosthesis having a first end configured to be positioned abutting an opening in the semicircular canal;

an actuator configured to receive electrical signals representing the input signal and configured to vibrate in response to the electrical signals, and a coupler connecting the actuator to the stapes prosthesis such that vibration of the actuator results in waves of fluid motion in a recipient's semicircular canal.

4. The system of claim 1, wherein the stimulation arrangement comprises:

an actuator configured to receive electrical signals representing the input signal and configured to vibrate in response to the electrical signals;

a stapes prosthesis having first and second ends, the first end having a surface configured to be positioned abutting the round window in the recipient's cochlea, and wherein the first end surface is substantially orthogonal to a longitudinal axis extending through the actuator; and an elongate rod extending longitudinally from the actuator connecting the actuator to the stapes prosthesis such that vibration of the actuator results in waves of fluid motion in a recipient's scala tympani.

5. The system of claim 1, wherein the stimulation arrangement comprises:

an actuator configured to receive electrical signals representing the input signal and configured to vibrate in response to the electrical signals, wherein the actuator is coupled to the recipient's ossicular chain, and wherein the ossicular chain delivers the vibration to the recipient's inner ear.

6. The system of claim 1, further comprising:

a sense amplifier that receives signals from the first and second electrical contacts that represent the detected neural response.

7. The system of claim 1, wherein the processor executes algorithms that assess the neural response by comparing the response to a target neural response.

8. The system of claim 1, wherein the processor adjusts the operation of the hearing prosthesis to provide equal loudness of all input signals received across an audible frequency range.

9. The system of claim 1, wherein the processor adjusts the operation of the hearing prosthesis to improve speech perception by the recipient.

10. The system of claim 1, wherein the processor implements one or more safety guidelines which prevent adjustment of the hearing prosthesis to improve speech perception by the recipient.

11. A hearing prosthesis, comprising:

a stimulation arrangement that at least one of mechanically and acoustically stimulates the recipient to generate displacement of the fluid within the recipient's inner ear based on an input signal;

an on-board fitting system comprising:

at least first and second electrical contacts disposed on the outside of recipient's inner ear to detect a neural response of the recipient's auditory nerves to the displacement of the fluid within the recipient's inner ear; and a processor that assesses the recipient's, neural response in real-time and adjusts operation of the hearing prosthesis based on the assessment of the neural response.

12. The prosthesis of claim 11, wherein the stimulation arrangement comprises:

an audio output device that generates an amplified audio signal representing the input signal.

13. The system of claim 11, wherein the stimulation arrangement comprises:

a stapes prosthesis having a first end configured to be positioned abutting an opening in the semicircular canal;

an actuator configured to receive electrical signals representing the input signal and configured to vibrate in response to the electrical signals, and a coupler connecting the actuator to the stapes prosthesis such that vibration of the actuator results in waves of fluid motion in a recipient's semicircular canal.

14. The prosthesis of claim 11, wherein the stimulation arrangement comprises:

a stapes prosthesis having a first end configured to be positioned abutting an opening in the semicircular canal;

an actuator configured to receive electrical signals representing the input signal configured to vibrate in response to the electrical signals, and a coupler connecting the actuator to the stapes prosthesis such that vibration of the actuator results in waves of fluid motion on a recipient's semicircular canal.

15. The prosthesis of claim 11, wherein the stimulation arrangement comprises:

an actuator configured to receive electrical signals representing the input signal and configured to vibrate in response to the electrical signals, wherein the actuator is coupled to the recipient's ossicular chain, and wherein the ossicular chain delivers the vibration to the recipient's inner ear.

16. The prosthesis of claim 11, further comprising:

a sense amplifier that receives signals from the first and second contacts representing the recipient's neural response.

17. The prosthesis of claim 11, wherein the processor assesses the neural responses by comparing the responses to target neural responses.

18. The prosthesis of claim 11, wherein the processor adjusts the operation of the hearing prosthesis to provide equal loudness of all input signals received across an audible frequency range.

19. The prosthesis of claim 11, wherein the processor adjusts the operation of the hearing prosthesis to improve speech perception by the recipient.

20. The prosthesis of claim 11, wherein the processor implements one or more safety guidelines which prevent adjustment of the hearing prosthesis that would result in stimulation damaging to the recipient's hearing.

* * * * *